United States Patent
Walter et al.

(10) Patent No.: US 7,259,285 B1
(45) Date of Patent: Aug. 21, 2007

(54) OLIGOMERIZATION CATALYST, A METHOD FOR PRODUCTION AND THE USE THEREOF

(75) Inventors: Marc Walter, Frankenthal (DE); Thomas Heidemann, Weinheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 532 days.

(21) Appl. No.: 10/129,981

(22) PCT Filed: Nov. 16, 2000

(86) PCT No.: PCT/EP00/11344

§ 371 (c)(1),
(2), (4) Date: May 13, 2002

(87) PCT Pub. No.: WO01/37989

PCT Pub. Date: May 31, 2001

(30) Foreign Application Priority Data

Nov. 27, 1999 (DE) ................. 199 57 173

(51) Int. Cl.
*C07C 2/24* (2006.01)
*C07C 2/10* (2006.01)
*C07C 2/16* (2006.01)
*B01J 27/02* (2006.01)
*B01J 27/053* (2006.01)

(52) U.S. Cl. ............ 585/513; 585/512; 585/515; 585/520; 585/526; 585/531; 585/533; 502/216; 502/217; 502/221; 502/222

(58) Field of Classification Search ........... 585/513, 585/512, 515, 520, 526, 531, 533; 502/216, 502/217, 221, 222
See application file for complete search history.

(56) References Cited

U.S. PATENT DOCUMENTS

| | | | | |
|---|---|---|---|---|
| 2,794,842 A | 6/1957 | Hogan et al. | ............ | 260/683 |
| 3,959,400 A | 5/1976 | Lucki | ............ | 260/683 |
| 4,511,750 A | 4/1985 | Miller | ............ | 585/526 |
| 5,177,282 A | 1/1993 | Nierlich et al. | ............ | 585/329 |
| 5,849,972 A | 12/1998 | Vicari et al. | ............ | 585/531 |
| 5,883,036 A | 3/1999 | Fujie et al. | ............ | 502/217 |

FOREIGN PATENT DOCUMENTS

| | | |
|---|---|---|
| DE | 39 14 817 | 7/1995 |
| EP | 0 272 970 | * 6/1998 |
| FR | 2 641 477 | 7/1990 |
| JP | 73/85506 A | 11/1973 |
| JP | 74/3489 B | 1/1974 |
| JP | 98/101586 A | 4/1998 |
| WO | WO95/14647 | 6/1995 |
| WO | WO 95/14647 | 6/1995 |

OTHER PUBLICATIONS

Handbook of Heterogeneous Catalysts vol. 1 pp. 72-86.

* cited by examiner

*Primary Examiner*—Elizabeth D. Wood
(74) *Attorney, Agent, or Firm*—Novak Druce & Quigg, LLP

(57) ABSTRACT

An oligomerization catalyst for olefins having from 2 to 6 carbon atoms is produced by treating aluminum oxide with a nickel compound and a sulfur compound, either simultaneously or firstly with the nickel compound an then with the sulfur compound, and subsequently drying and calcining the resulting catalyst, wherein a molar ratio of sulfur to nickel in the finished catalyst of from 0.25:1 to 0.38:1 is set in this way. The catalyst and its use are also described.

3 Claims, No Drawings

OLIGOMERIZATION CATALYST, A METHOD FOR PRODUCTION AND THE USE THEREOF

The present invention relate to a process for producing an oligomerization catalyst for olefins having from 2 to 6 carbon atoms, in which aluminum oxide is treated with a nickel compound and a sulfur compound, either simultaneously or firstly with the nickel compound and then with the sulfur compound, and the resulting catalyst is subsequently dried and calcined.

The invention further relates to the catalysts produced in this way and to a process for preparing oligomers of olefins having from 2 to 6 carbon atoms or of mixtures of these olefins.

Olefins having from 2 to 6 carbon atoms and their mixtures, in particular olefins having 4 carbon atoms, are available in large quantities both from FCC plants and from steam crackers. The respective $C_4$ fraction, i.e. the mixture of butenes and butanes, is, after the isobutene has been separated off, very well suited to the preparation of oligomers, in particular octenes and dodecenes. Both the octenes and dodecenes are, after hydroformylation and subsequent hydrogenation to give the corresponding alcohols, used, for example, for the preparation of plasticizers or surfactant alcohols.

For use as plasticizer alcohol, the degree of branching plays a decisive roll in determining the properties of the plasticizer. The degree of branching is described by the ISO index, which indicates the mean number of methyl branches in the respective fraction. Thus, for example, n-octenes with 0, methylheptenes with 1 and dimethylhexenes with 2 contribute to the ISO index of a fraction. The lower the ISO index, the more linear the molecules in the respective fraction. The higher the linearity, i.e. the lower the ISO index, the higher the yields in the hydroformylation and the better the properties of the plasticizer prepared therewith. A low ISO index results in plasticizers, for example, being less volatile, and PVC containing such plasticizers displays improved fracture behavior when cold.

The oligomerization is carried out industrially in the presence of either homogeneous or heterogeneous catalysts.

For the heterogeneously catalyzed oligomerization, nickel- and sulfur-containing aluminum oxide catalysts are already known in the prior art. JP-B 74/3489 (Nippon Oil Co. Ltd.) describes the use of nickel sulfide on aluminum oxide as catalyst for the preparation of lower olefin polymers.

In many cases, nickel and sulfate are applied in the form of nickel sulfate to the support, which normally results in Ni:S ratios of about 1 in the finished catalyst: U.S. Pat. No. 2,794,842 (Phillips Petroleum Co.) disclosed the polymerization of olefins using nickel sulfate on an aluminum oxide support. U.S. Pat. No. 3,959,400 (Mobil Oil Corp.) describes a process in which the catalytic dimerization of olefins having from 2 to 4 carbon atoms is carried out over aluminum oxides which have been coated with nickel sulfate. FR-A 2 641 477 (Institut Français du Pétrole) teaches the dimerization of olefins by means of an aluminum oxide which has been treated with nickel sulfate. U.S. Pat. No. 4,511,750 (Chevron Research Co.) describes the oligomerization of lower olefins by means of nickel sulfate on a porous inorganic oxide, for example aluminum oxide.

JP-A 73/85506 (Koa Sekiyu K.K.) discloses a process for preparing octenes which comprises using a catalyst based on nickel oxide/silicon dioxide, nickel oxide/aluminum oxide or nickel oxide/silicon dioxide/aluminum oxide, to which a metal salt has been added. This metal salt may be a sulfate.

Catalysts whose Ni:S ratios deviate from 1 are likewise known:

U.S. Pat. No. 5,883,036 (Koa Oil Co. Ltd.) and JP-A 98/101586 teach the production of an aluminum oxide treated with sulfate ions and nickel oxide as catalyst for the oligomerization of olefins. The aluminum oxide is doped with the sulfate ions before it is doped with the nickel oxide.

EP-B 272 970 (Institut Français du Pétrole) discloses a process for the dimerization of monoolefinic hydrocarbons, in which an aluminum oxide having a particular content of sulfate ions and containing from 0.5 to 15% by weight of nickel is used. Furthermore, the molar ratios of sulfur to nickel in the catalyst are from 0.4:1 to 0.8:1. In the production of this catalyst, the source of sulfate ions and the source of nickel ions are allowed to act simultaneously on the aluminum oxide, followed by drying and calcination, or, alternatively, the aluminum oxide is treated with a nickel salt which can be decomposed by heat and the doped support is dried and calcined, followed by application of the sulfate ions.

The dimer selectivity and the degree of branching of the alkyl chains in the olefin oligomers prepared using the known catalysts based on sulfur- and nickel-containing aluminum oxides is, however, not yet satisfactory.

It is an object of the present invention to provide catalysts of this type which enable higher dimer selectivity and higher degrees of linearity of the alkyl groups to be achieved at good olefin conversions.

We have found that this object is achieved by a process for producing an oligomerization catalyst for olefins having from 2 to 6 carbon atoms, in which aluminum oxide is treated with a nickel compound and a sulfur compound, either simultaneously or firstly with the nickel compound and then with the sulfur compound, and the resulting catalyst is subsequently dried and calcined, wherein a molar ratio of sulfur to nickel in the finished catalyst of from 0.25:1 to 0.38:1 is set in this way.

In addition, we have found the novel catalysts obtainable in this way and a process for preparing oligomers of olefins having from 2 to 6 carbon atoms or of mixtures of these olefins.

For the purposes of the present invention, "oligomers" are dimers, trimers and higher oligomers of the olefins having from 2 to 6 carbon atoms. The process of the present invention is particularly suitable for preparing dimers of these olefins.

The catalyst of the present invention can be produced in various ways, for example by a) coprecipitation of solutions in which the catalyst constituents are present in dissolved form: the precipitate is washed, dried, shaped and calcined (cf., for instance, DE-A 43 39 713), or b) impregnation of the aluminum oxide, which is in the form of powder or has already been shaped, with a solution of the nickel compound and the sulfur compound and subsequent drying and calcination of the product obtained.

The catalysts of the present invention are preferably produced by variant b) using prefabricated shaped aluminum oxide bodies, for example spheres and especially extrudates or star extrudates having a largest diameter of from 1 to 3 mm. The above indication of size is merely by way of example and does not restrict the scope of the present invention. The aluminum oxide support is obtained in discrete, shaped form by shaping the aluminum oxide precursor or the powder obtained therefrom by calcination in a manner known per se so as to meet the respective requirements (cf. Handbook of Heterogenous Catalysis, Vol. 1, page 80 ff.).

The chemical and physical properties of the aluminum oxides used for producing the catalyst are known to depend greatly on the origin of the aluminum oxides. They are obtainable in a manner known per se and are also commercially available. They are obtained, for instance, by calcination of aluminum oxide precursors such as boehmite and hydrargillite.

For producing the catalysts of the present invention, preference is given to using γ-aluminum oxide, η-aluminum oxide and also mixtures thereof, as are commercially available from, for example, BASF, Condea, Alcoa, Grace and Rhone-Poulenc. Preference is given to aluminum oxide supports which consist predominantly or especially entirely of γ-aluminum oxide. These aluminum oxides preferably have a water absorption capacity of more than 0.4 ml/g and a BET surface area of more than 150 m$^2$/g. Furthermore, preference is given to using such aluminum oxides containing less than 0.2% by weight of $Na_2O$. Preference is also given to using such aluminum oxides containing less than 0.2% by weight of $Fe_2O_3$.

The aluminum oxide is particularly advantageously treated with the nickel compound and the sulfur compound by impregnation with solutions of these compounds.

In the impregnation, the sulfur compound and the nickel compound are preferably used as their solution, in particular in water and less preferably in organic polar solvents, e.g. alcohols such as methanol and ethanol, or mixtures of the suitable solvents.

Suitable sulfur compounds are sulfates and all compounds of sulfur which can be converted into sulfate on heating in the presence of oxygen or of oxygen-containing gas mixtures such as air under the calcination conditions, for example the sulfides. Preference is given to using water-soluble sulfates such as ammonium sulfate which decomposes at about 250° C. and especially sulfuric acid.

Suitable nickel compounds are all compounds of nickel which can converted into an oxidic form of the metal on heating in the presence of oxygen or of oxygen-containing gas mixtures such as air under the calcination conditions. As nickel compound, preference is given to using water-soluble nickel salts, for example those having an organic anion such as the formate, oxalate, acetylacetonate or the 2-ethylhexanoate and especially hydrated or anhydrous nickel nitrate.

In the impregnation, the aluminum oxide is preferably stirred with a solution comprising exactly those molar amounts of nickel compound and sulfur compound with which the aluminum oxide is to be doped. The volume of the solution is advantageously chosen so that it just corresponds to the water absorption capacity of the aluminum oxide.

Alternatively, the nickel compound and the sulfur compound can be applied by a plurality of impregnation steps, after each of which the catalyst precursor obtained is dried.

If, according to the present invention, the sulfur compound is applied to the aluminum oxide only after application of the nickel compound, the aluminum oxide which has been treated with the nickel compound is preferably dried beforehand at from 50 to 200° C.

Otherwise, the impregnation of the aluminum oxide is carried out in a manner known per se (cf., for instance, EP-B 272 970).

The impregnated catalyst is subsequently dried, preferably in air at from 50 to 200° C.

Calcination is carried out in an oxygen-containing atmosphere, preferably in air. The calcination temperature is normally in the range from 300 to 600° C. During the calcination, the catalytically active oxidic nickel- and sulfur-containing composition is formed from the nickel compound and the sulfur compound.

If, contrary to the invention, firstly the sulfur compound and then the nickel compound are allowed to act on the aluminum oxide, undesirably high ISO indices are obtained in the oligomerization.

The novel catalysts produced in this way are advantageously conditioned in a stream of dry nitrogen, e.g. at atmospheric pressure and temperatures of from 20 to 500° C., preferably from 100 to 250° C., to remove traces of moisture (for instance from the air) from the catalyst prior to use in the oligomerization.

The molar ratio of sulfur to nickel in the catalyst of the present invention determined by means of elemental analysis is preferably from 0.28:1 to 0.35:1. Above this range, the dimer selectivity normally decreases significantly, while below this range, the catalyst activity generally decreases significantly.

The oligomerization process of the present invention is particularly suitable for mixtures of olefins having 3 or 4 carbon atoms. It is especially suitable for the conversion of mixtures comprising olefins having 4 carbon atoms, in particular hydrocarbon streams which comprise 1-butene and/or 2-butene and butane and are essentially free of isobutene, into dodecenes and, in particular, into octenes. Suitable hydrocarbon streams comprising olefins having 4 carbon atoms are, for example, mixtures having the following composition:

| butanes | from 10 to 90% by weight |
|---|---|
| butenes | from 10 to 90% by weight, | where the butene fraction may have the following composition:

| 1-butene | from 1 to 50% by weight, |
|---|---|
| cis-2-butene | from 1 to 50% by weight, |
| trans-2-butene | from 1 to 99% by weight, |
| isobutene | from 1 to 5% by weight. |

A particularly preferred starting material is raffinate II. This is a butene-containing $C_4$-hydrocarbon mixture as is obtained from the $C_4$ fraction of crackers after more highly unsaturated hydrocarbons such as diolefins, in particular 1,3-butadiene, or acetylene and then the isobutene present have been separated off. A typical composition of raffinate II is, for example:

| isobutane, n-butane | 26% by weight, |
|---|---|
| isobutene | 1% by weight, |
| 1-butene | 26% by weight, |
| trans-2-butene | 31% by weight, |
| cis-2-butene | 16% by weight. |

The $C_4$-hydrocarbon streams can, for example, be freed of butadiene, sulfur-containing and oxygen-containing compounds such as alcohols, aldehydes, ketones or ethers in a manner known per se from, for instance, DE-A 39 14 817 by selective hydrogenation or absorption on molecular sieves.

The oligomerization reaction preferably takes place at from 20 to 280° C., in particular from 30 to 120° C., and a pressure of preferably from 10 to 300 bar and in particular from 20 to 70 bar. The pressure is advantageously selected so that the hydrocarbon feed mixture is present in a liquid or supercritical state at the temperature set. The reactor is generally a cylindrical reactor which is charged with the catalyst and through which the liquid reaction mixture flows, for example, from the top downward. The oligomerization process of the present invention can be carried out to the desired final conversion of the butenes in a single reactor, in which case the oligomerization catalyst may be arranged in one or more fixed beds in the reactor. Alternatively, the process of the present invention can be carried out using a reactor cascade comprising two or more, preferably two, reactors connected in series; it is possible for the oligomerization of the hydrocarbons in the reaction mixture to be carried out to only a partial conversion when passing though the reactor or reactors upstream of the last of the cascade and for the desired final conversion to be achieved only when the reaction mixture passes through the last reactor of the cascade. In the individual reactors of the reactor cascade, the oligomerization catalyst can be arranged in one or more fixed catalyst beds. Furthermore, different reaction conditions in respect of pressure and/or temperature within the abovementioned pressure and temperature ranges can be set in the individual reactors of the reactor cascade. It is also possible to use different oligomerization catalysts in the individual reactors of the cascade, although the use of the same catalyst in all reactors of the cascade is preferred.

A single-stage reaction zone is spoken of when a single oligomerization reactor is used or when use is made of a reactor cascade in whose reactors the same oligomerization catalyst is used.

If different oligomerization catalysts are employed in the individual reactors of the cascade, this is referred to as a multistage reaction zone.

The oligomerization can be carried out under supercritical conditions in respect of the starting material, in which case it is preferred that no additional solvents which are not in the supercritical state are employed.

After leaving the single-stage or multistage reaction zone, the oligomers formed are separated in a manner known per se from the unreacted hydrocarbons and all or most of these hydrocarbons are recirculated in a manner known per se (cf., for instance, WO-A 95/14647).

The oligomerization process of the present invention can be carried out adiabatically or isothermally.

In the engineering sense, adiabatic reaction conditions or mode of operation means reaction conditions or mode of operation in which, apart from the part of the heat of reaction which passes from the reactor to the surroundings by natural heat conduction and heat radiation, all of the heat of reaction is taken up by the reaction mixture and carried from the reactor by this.

In contrast, in isothermal reaction conditions in the engineering sense, the heat of reaction is deliberately removed from the reactor by means of cooling or thermostating facilities beyond the degree to which it would be lost by natural heat conduction or heat radiation; the heat of reaction is generally firstly taken up by a heat transfer medium, the coolant, before it is passed to the surroundings or, for example when using heat exchangers, utilized for heating materials or for energy recovery (cf., for instance, WO-A 95/14647).

The oligomers are separated in a manner known per se, especially by fractional distillation, in particular to give the desired octene and dodecene fractions which serve as starting materials for the hydroformylation for preparing the plasticizer alcohols nonanol and tridecanol. Owing to the low branching of the starting oligomers, the higher alcohols prepared therefrom have excellent properties for the preparation of plasticizers and surfactants.

EXAMPLES

I. Catalysts

The catalysts were produced using the γ-aluminum oxide supports listed in Table 1.

γ-aluminum oxide used was the grade "D10-10" from BASF or the grade "Pural" from Condea.

TABLE 1

γ-Aluminum oxide supports used for producing the catalysts

| Cat. des* | Shape | Water uptake capacity [ml/g] | Bulk density [g/l] | Loss on ignition [% by weight at 1 h and 900° C.] | BET surface area [m²/g] |
|---|---|---|---|---|---|
| A | 1.5 mm extrudates | 0.45 | 760 | 7.6 | 255 |
| B | 1.5 mm extrudates | 0.60 | 661 | 1.8 | 280 |
| C | 3 mm star extrudates | 0.76 | 530 | 1.6 | 202 |
| D | 1.5 mm extrudates | 0.65 | 661 | 1.8 | 280 |

*Catalyst designation

General Method of Producing Catalysts (the Associated Numerical Values May be Found in Table 2 Below)

The $Ni(NO_3)_2 \cdot 6H_2O$ used was from Fluka.

To produce the catalysts, the respective support was impregnated at room temperature with a solution comprising the amounts indicated below of 96% strength $H_2SO_4$, 97% pure $Ni(NO_3)_2 \cdot 6H_2O$ and water while stirring. The catalyst obtained in this way was dried in air for 10 hours at 120° C. and calcined in air for 2 hours at 500° C. The percentages of nickel ("Ni") and of sulfur ("S") based on the total weight of the catalyst obtained and also the molar ratio of sulfur to nickel ("S:Ni") in the catalyst were then determined.

The sulfur content of the finished catalyst was determined by quantitative infrared analysis of the sulfur dioxide formed on "combustion" of the catalyst. The nickel content could be measured by ICP-mass spectrometry.

TABLE 2

Catalysts IC1-IC4 according to the present invention

| | | | Impregnation solution | | | | | |
|---|---|---|---|---|---|---|---|---|
| No. | Support | Amount of support [g] | $H_2SO_4$ [mmol] | $Ni(NO_3)_2 \cdot 6H_2O$ [mmol] | Total volume of the solution [ml] | S [% by weight] | Ni [% by weight] | S:Ni |
| IC1 | A | 190 | 92 | 322 | 86 | 1.42 | 9.08 | 0.29 |
| IC2 | B | 200 | 112 | 361 | 115 | 1.54 | 9.08 | 0.31 |

TABLE 2-continued

Catalysts IC1-IC4 according to the present invention

| | | Impregnation solution | | | | | |
|---|---|---|---|---|---|---|---|
| No. | Support | Amount of support [g] | $H_2SO_4$ [mmol] | $Ni(NO_3)_2 \cdot 6H_2O$ [mmol] | Total volume of the solution [ml] | S [% by weight] | Ni [% by weight] | S:Ni |
| IC3 | C | 200 | 125 | 361 | 125 | 1.67 | 9.04 | 0.34 |
| IC4 | C | 200 | 132 | 125 | 1.80 | 9.02 | 0.37 | |

TABLE 3

Comparative catalysts CC1-CC4

| | | Impregnation solution | | | | | |
|---|---|---|---|---|---|---|---|
| No. | Support | Amount of support [g] | $H_2SO_4$ [mmol] | $Ni(NO_3)_2 \cdot 6H_2O$ [mmol] | Total volume of the solution [ml] | S [% by weight] | Ni [% by weight] | S:Ni |
| CC1 | D | 200 | 83 | 361 | 125 | 1.13 | 9.10 | 0.23 |
| CC2 | C | 200 | 160 | 361 | 125 | 2.20 | 9.00 | 0.45 |
| CC3 | D | 200 | 181 | 361 | 125 | 2.38 | 8.99 | 0.49 |
| CC4 | C | 200 | 230 | 361 | 125 | 3.15 | 9.00 | 0.64 |

Comparative Catalyst CC5 (Sulfate Applied Before Nickel)

380 g of support A were impregnated at room temperature with 171 ml of a solution comprising 184 mmol of $H_2SO_4$ (96% strength) and water while stirring. The product was dried in air for 3 hours at 120° C. and calcined in air for 2 hours at 500° C. The catalyst obtained in this way was subsequently impregnated at room temperature with 171 ml of a solution comprising 644 mmol of $Ni(NO_3)_2.6H_2O$ (97% pure) and water while stirring. The catalyst obtained in this way was then dried in air for 2 hours at 120° C. and calcined in air for 2 hours at 500° C. The percentage of nickel was subsequently determined as 9.01% by weight and that of sulfur was determined as 1.40% by weight and the molar ratio of sulfur to nickel was found to be 0.28.

II. Oligomerizations

The feed stock used for the oligomerization of butenes was "raffinate II" of the following composition:

29.8% by weight of 1-butene 31.7% by weight of trans-2-butene 17.8% by weight of cis-2-butene 2.1% by weight of isobutene 15.3% by weight of n-butane 3.1% by weight of isobutane 0.2% by weight of isopentane The reaction was carried out continuously in a thermostated tube reactor whose reaction tube had an internal diameter of 30 mm. The reaction pressure which was above the intrinsic pressure of the raffinate II was generated by means of an upstream reactor feed pump and was regulated by means of customary pressure maintenance devices downstream of the reactor. 1500 standard l/h of dry nitrogen were firstly passed over 165 ml of the catalyst in the reaction tube for 24 hours at 160° C. The reaction tube together with the catalyst were subsequently allowed to cool under nitrogen to 20° C. The temperature was then increased to 80° C. over a period of 24 hours at a raffinate II pressure of 20 bar and the reaction was carried out under these conditions and a weight hourly space velocity of 3.35 kg of raffinate II per liter of catalyst and hour. The reaction product was isolated and the proportion of isomers having 8 carbon atoms ("$C_8$ selectivity") and the ISO index of the $C_8$ fraction were determined by means of gas chromatography. Table 3 shows the results.

TABLE 3

Results of the oligomerizations

| No. | Catalyst | S:Ni | Conversion of butenes [% by weight] | $C_8$ selectivity [% by weight] | ISO index |
|---|---|---|---|---|---|
| 1 | IC1 | 0.29 | 34 | 91 | 1.11 |
| 2 | IC2 | 0.31 | 42 | 90 | 1.05 |
| 3 | IC3 | 0.34 | 35 | 90 | 1.06 |
| 4 | IC4 | 0.37 | 34 | 91 | 1.09 |
| 5 | CC1 | 0.23 | <5 | Not determined | Not determined |
| 6 | CC2 | 0.45 | 38 | 87 | 1.11 |
| 7 | CC3 | 0.49 | 36 | 85 | 1.12 |
| 8 | CC4 | 0.64 | 37 | 86 | 1.27 |
| 9 | CC5* | 0.28 | 28 | 89 | 1.25 |

*Sulfate applied before nickel

The invention claimed is:

1. A process for preparing oligomers, said process comprising contacting hydrocarbon streams comprising olefins having from 4 to 6 carbon atoms or mixtures of these olefins at from 20 to 280° C. and a pressure of from 10 to 300 bar with a catalyst said catalyst being obtained by treating γ-aluminum oxide with a nickel compound and a sulfur compound, either simultaneously or firstly with the nickel compound and then with the sulfur compound, and subsequently drying and calcining the treated γ-aluminum oxide, wherein a molar ration of sulfur to nickel in the finished catalyst of from 0.25:1 to 0.38:1 is set in this way.

2. A process as claimed in claim 1, wherein the olefins used have 4 carbon atoms.

3. A process as claimed in claim 2, wherein said hydrocarbon streams comprise a mixture of 1-butene and/or 2-butene and butane and are essentially free of isobutene.

* * * * *